(12) United States Patent
Zen et al.

(10) Patent No.: US 7,393,504 B2
(45) Date of Patent: Jul. 1, 2008

(54) FLOW INJECTION ELECTROCHEMICAL DETECTING DEVICE

(75) Inventors: Jyh-Myng Zen, No. 169, Tali 2 St., Tali, Taichung Hsien (TW); Cheng-Teng Hsu, Tali (TW); Hsieh-Hsun Chung, Tali (TW); Chun-Mu Huang, Tali (TW); Tung-Meng Tsai, Tali (TW); Hueih-Jing Lyuu, Tali (TW)

(73) Assignee: Jyh-Myng Zen, Hsien (TW)

( * ) Notice: Subject to any disclaimer, the term of this patent is extended or adjusted under 35 U.S.C. 154(b) by 881 days.

(21) Appl. No.: 10/681,160

(22) Filed: Oct. 9, 2003

(65) Prior Publication Data
US 2005/0079100 A1     Apr. 14, 2005

(51) Int. Cl.
*G01N 27/00*     (2006.01)
*G01N 21/00*     (2006.01)
*G01N 27/26*     (2006.01)

(52) U.S. Cl. .................. 422/82.01; 422/52; 422/55; 436/150; 204/400; 204/229.1; 204/228.9; 204/229.9

(58) Field of Classification Search .................. 422/58, 422/82; 220/918
See application file for complete search history.

(56) References Cited

U.S. PATENT DOCUMENTS 5,826,718 A * 10/1998 Ahern et al. ................. 206/372
6,200,531 B1 * 3/2001 Liljestrand et al. ............ 422/52

* cited by examiner

*Primary Examiner*—Jill Warden
*Assistant Examiner*—Neil Turk
(74) *Attorney, Agent, or Firm*—Lowe Hauptman Ham & Berner, LLP

(57) ABSTRACT

A flow injection electrochemical detecting device has a base (10), a cover pivotally mounted on the base (10), and a locking device attached between the base (10) and the cover (20). The base (10) has a recess (12) defined in a top to accommodate a working electrode inside the recess (12). An annular trench (28) in a bottom partially receives an O-ring (282) serving as a separator to form a space between the base (10) and the cover (20). Multiple channels are defined through the cover (20) to communicate with the space. Therefore, a flow injection electrochemical detecting device is achieved. By pivotally attaching the cover (20) on the base (10) and using the locking device, the detecting device is easily opened or closed to change the working electrode (50) in a convenient way.

7 Claims, 9 Drawing Sheets

FLOW INJECTION ELECTROCHEMICAL DETECTING DEVICE

BACKGROUND OF THE INVENTION

1. Field of the Invention

The present invention relates to an electrochemical detecting device for a fluid, and more particularly to an electrochemical detecting device in which an electrode can be changed quickly and easily.

2. Description of Related Art

An electrochemical detecting device is a burgeoning object in chemical studies and has high scientific value to provide considerable economical benefits, because the electrochemical detecting device is widely applied in various fields of science and technology. A good detecting device needs to have excellent selectivity, sensitivity, and short detecting time and further have excellent stability and reliability. In order to reduce the quantity of testing samples as less as possible in the electrochemical detecting device and also to simplify the operational procedure, the electrochemical detecting device is minimized in size and designed to satisfy these requirements. Additionally, the electrochemical detecting device can be easily combine with various electrodes to the trace analysis in different fields such as bio-chemistry, environmental estimation, drug control, cosmetic control etc. It can also combine with flow injection analysis (FIA), high performance liquid chromatography (HPLC), or capillary electrophoresis (CE) to increase the sensitivity in detection.

With reference to FIG. 9, a conventional electrochemical detecting device comprises a base (60), a cover (70), a working electrode (80) and a compartment layer (90).

The base (60) has a top (not numbered) and two positioning holes (62) vertically defined through the base (60). The working electrode (80) is mounted on the top of the base (60) and has two through holes (82) respectively aligning with the positioning holes (62) of the base (60). An inner lead (83) and an outer lead (84) electrically connect with each other and are attached on the working electrode (80) between the two through holes (82).

The compartment layer (90) is mounted on the working electrode (80) and also has two through holes (92) respectively aligning with the positioning holes (62). A rectangular channel (94) is defined between the two through holes (92) in the compartment layer (90) and accommodates the inner lead (83) inside the rectangular channel (94).

The cover (70) is mounted on the compartment layer (90) and has a bottom (not numbered) and two posts (76) extending from the bottom to respectively penetrate through the through holes (92, 82) of the compartment layer (90) and the working electrode (80). Two bolts (762) are respectively attached to the posts (76) to firmly clamp the working electrode (80) and the compartment layer (90) between the cover (70) and the base (60). Whereby, the channel (94) of the compartment layer (90) defines a space (not numbered) for liquid. An inlet (72) and an outlet (74) are defined in the cover (70) to communicate with the space for entry or exit of the liquid.

When the electrochemical detecting device operates, the detected liquid is injected into the space via the inlet (72) and the outer lead (84) is electrically connected with a readout system. Whereby, the inner lead (83) enables transmission of chemical data (for example: capacitance) to the readout system via the outer lead (84).

However, the conventional electrochemical detecting device still has some drawbacks in operation caused from the structure. For example, changing the working electrode (80) is troublesome since the bolts (762) have to be individually detached from the posts (76) to take the working electrode (80) out when assembling or disassembling the device. More particularly, if the working electrode (80) is disposable in nature, it has to be changed very often. Additionally, the working electrode (80) and the compartment layer (90) both must be punched to define through holes (82, 92) to allow the posts (76) to penetrate there through which also causes more trouble in the manufacturing processes.

The present invention has arisen to mitigate or obviate the disadvantages of the conventional electrochemical detecting device.

SUMMARY OF THE INVENTION

The first objective of the present invention is to provide a flow injection electrochemical detecting device, which is easily operated to change working electrodes.

The second objective of the present invention is to provide a flow injection electrochemical detecting device, which is enabled to cooperate with various electrodes accessories to work in different systems.

Further benefits and advantages of the present invention will become apparent after a careful reading of the detailed description with appropriate reference to the accompanying drawings.

DETAILED DESCRIPTION OF THE PREFERRED EMBODIMENT

Figure 1:
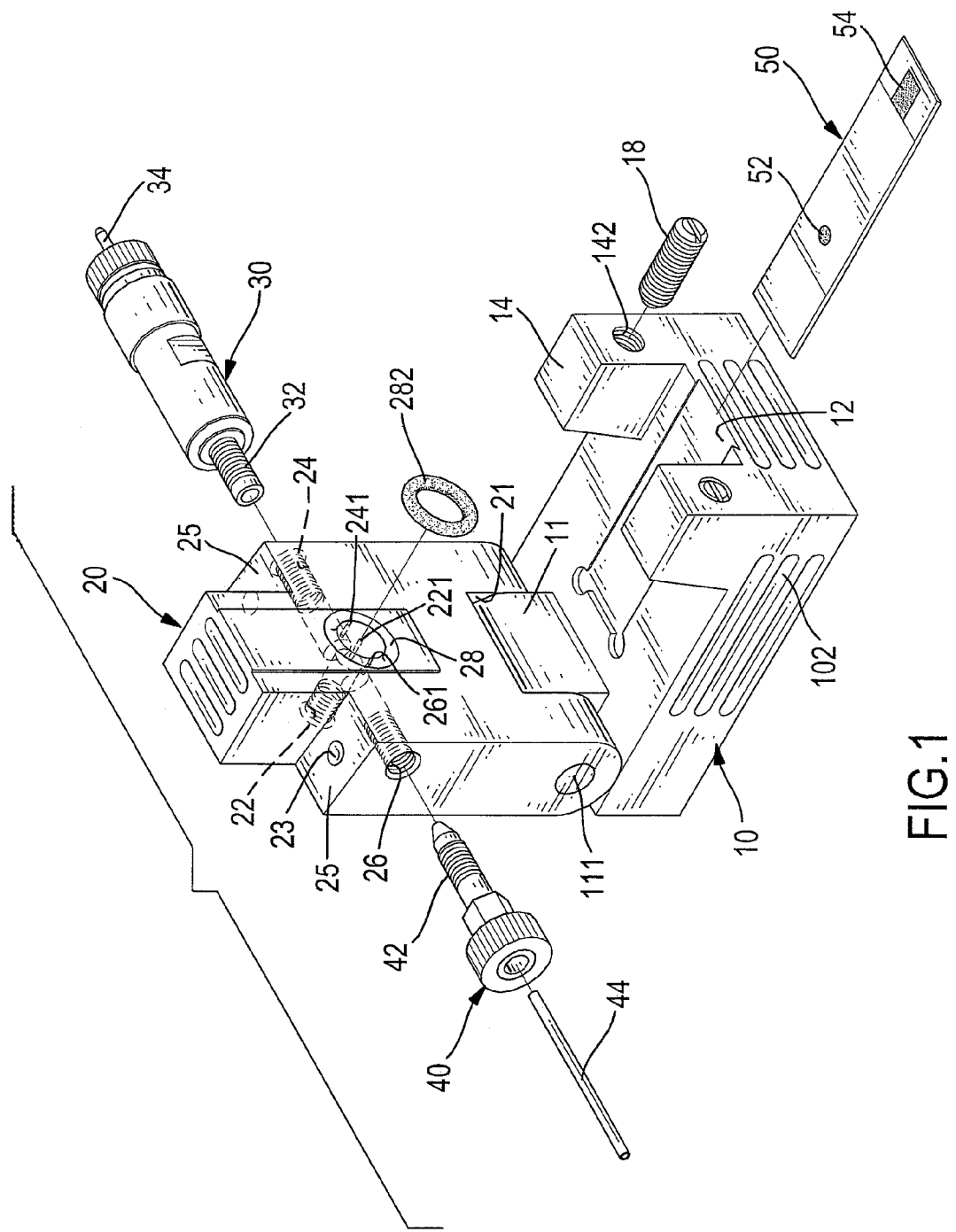
FIG. 1 is an exploded perspective view of a flow injection electrochemical detecting device in accordance with the present invention.
Figure 2:
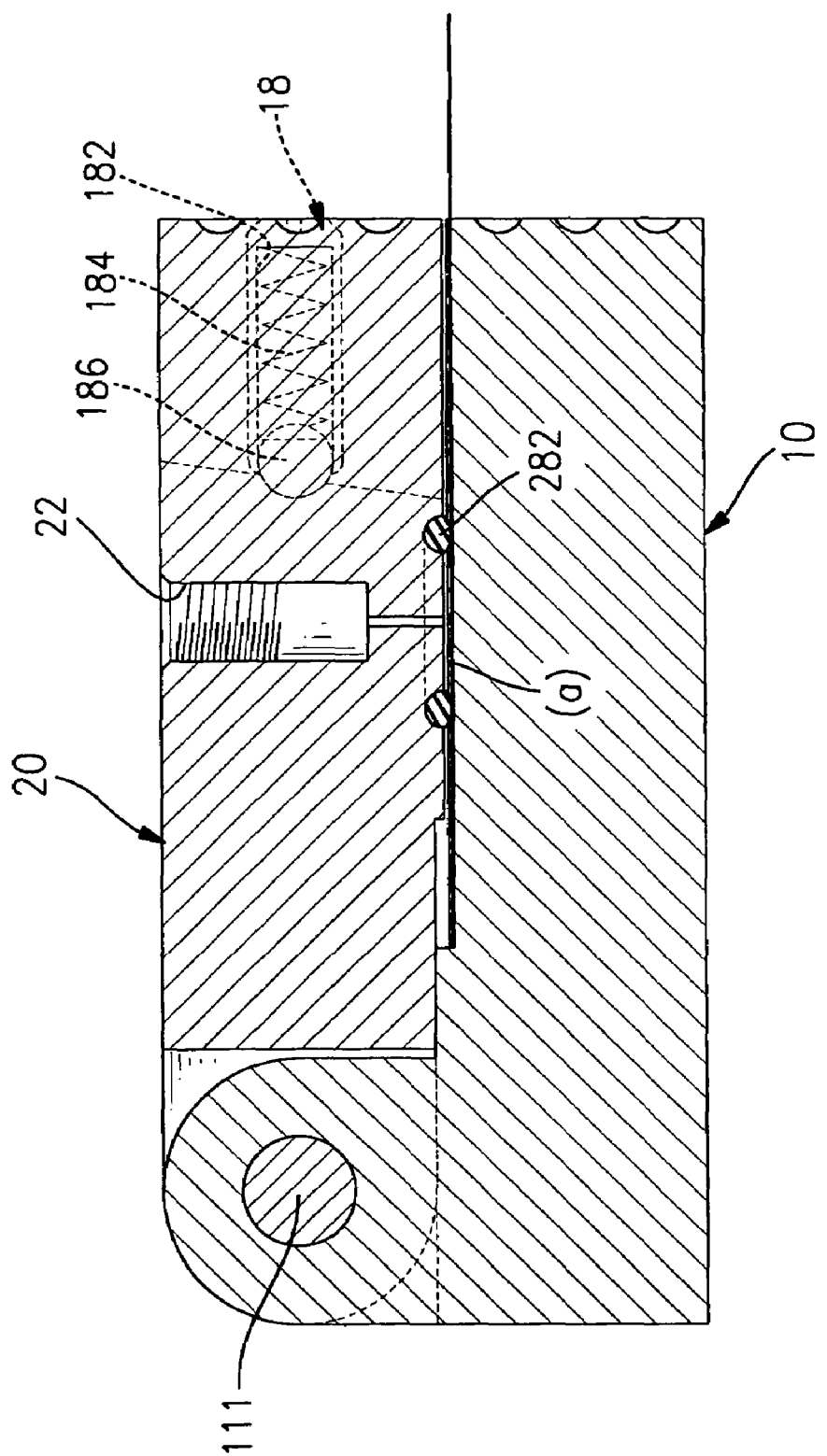
FIG. 2 is a cross-sectional side plane view of the flow injection electrochemical detecting device, wherein the device is closed.

With reference to FIGS. 1 and 2, a flow injection electrochemical detecting device in accordance with the present invention comprises a base (10), a cover (20) pivotally mounted on the base (10) and a locking device attached between the base (10) and the cover (20).

The base (10) is a quadratic prism and has a top (not numbered), four sides (not numbered), a front end (not numbered) and a rear end (not numbered). The base (10) has a recess (12) defined in the top and a pivotal post (11) formed near the rear end. Optionally, multiple anti-slip grooves (102) are defined in the four sides for a user to hold the base (10) easily. The recess (12) preferentially is a dovetail recess having a width tapering toward the top of the recess (12) so as to avoid a working electrode inside the recess (12) detaching from the top when the working electrode is attached on the cover (20).

The cover (20) pivotally attached on the top of the base (10) is also a substantially quadratic prism and has a top, a bottom, a front end, a rear end and two sides. The cover (20) has two side cutouts (25) defined at the front end, a resilient separator (not numbered) with an inner opening (not numbered), and multiple channels defined in the cover to extend to communicate with the inner opening of the resilient separator and each having an opening at an area within the annular trench (28). Preferentially, as shown in FIGS. 1 and 2, an annular trench (28) is defined in the bottom of the cover (20) and an O-ring (282) serves as the resilient separator partially received in the annular trench (28). An inlet (22) is defined through the cover (20) from the top to the bottom and has an opening (221) at an area within the annular trench (28). Moreover, a first outlet (24) and a second outlet (26) are defined respectively from opposed sides4 and each has an opening (241, 261) at the area within the annular trench (28). The cover (20) further has a cutout (21) defined at the rear end to receive the pivotal post (11) of the base (10), and a pin (111) penetrates the cover (20) at the cutout (21) and the pivotal post (11) to pivotally combine the cover (20) and the base (10). When the cover (20) is pressed downward to entirely mate with the base (10), the O-ring (282) defines a space (a) between the base (10) and the cover (20).

The locking device is attached between the base (10) and the cover (20) to close the detecting device tightly. The locking device is composed of two locating posts (14) each with a retractable ball (186) and erected on the top of the base (10). Two ball dents (23) are defined in peripheries of the side cutout (25) to align respectively with corresponding balls (186) on the locating posts (14). Preferentially, each locating post (14) has a threaded hole (142) defined in the locating post (14) and has a threaded rod (18) screwing into the threaded hole (142). The threaded rod (18) has a bore (182) defined axially to receive the ball (186) with a resilient element (184). The resilient element (184) provides a restitution force to the ball (186) to push the ball (186) to detachably engage and lock with the ball dent (23). By adjusting a depth of the threaded rod (18) going into the threaded hole (142), the tightness degree of the locking device is adjustable. Preferentially, the resilient element (184) is a spring. When the cover (20) closes on the base (10), the ball (186) engages with the ball dent (23) to lock the cover (20) on the base (10). Meanwhile, the O-ring (282) is clamped between the cover (20) and the base (10) and defines the space (a). When raising the cover (20), the cover (20) is pull upward to force the ball (186) to slightly move backward until separating from the dent (23). Therefore, the cover (20) is easily closed or opened in a convenient way of just moving the cover (20).

Figure 4:
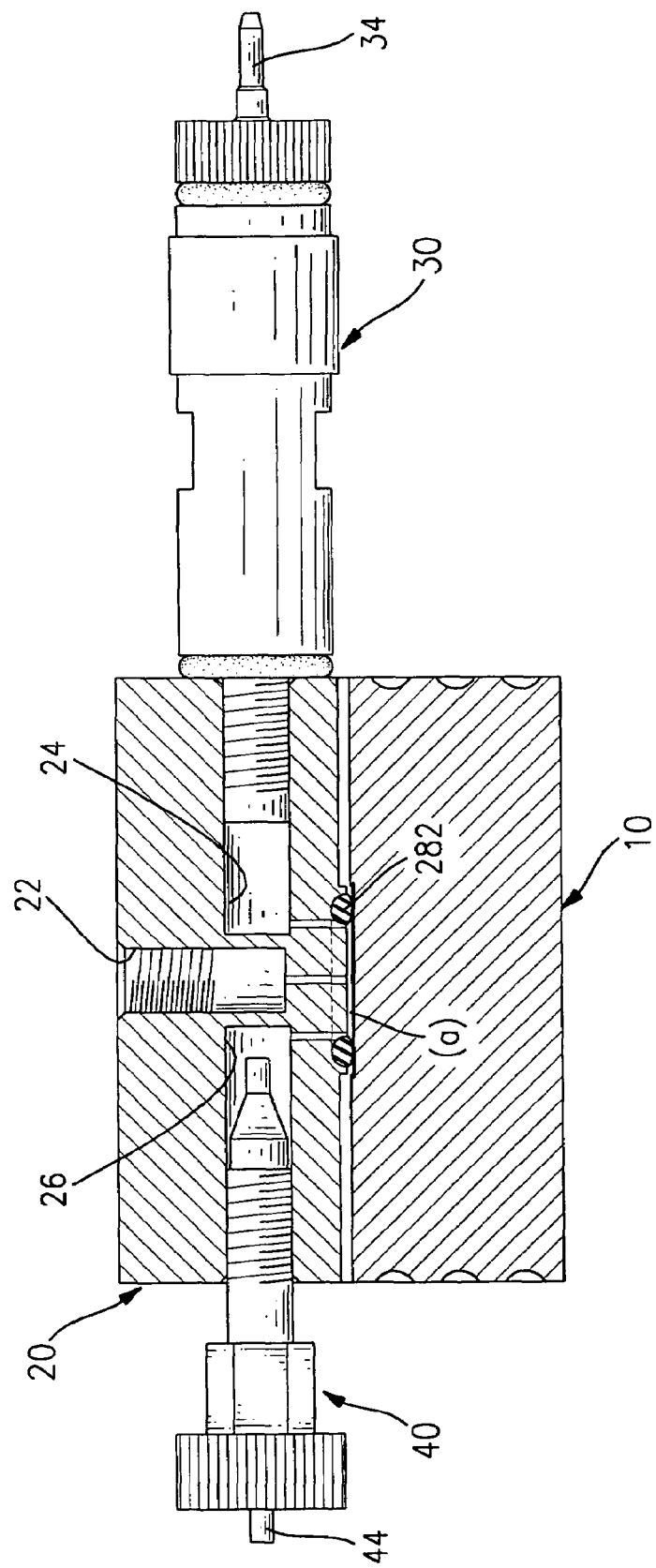
FIG. 4 is a cross-sectional front plane view of the flow injection electrochemical detecting device in FIG. 2.

With reference to FIGS. 1, 4 and 54, the flow injection electrochemical detecting device in the present invention needs other accessories when the device is operated. The accessories comprise a reference electrode (30), an auxiliary electrode (40), and a working electrode (50). The auxiliary electrode (40) and the reference electrode (30) have a first metal shaft (44) and a second metal shaft (34) respectively. The first metal shaft (44) is a hollow tube penetrating the auxiliary electrode (40) until reaching the inlet (22) to exhaust the liquid. The second metal shaft (34) is not hollow and is immovably attached at a rear end of the reference electrode (30) so that the second metal shaft (34) can not exhaust the liquid thereby. The reference electrode (30) and the auxiliary electrode (40) are selectively inserted into the first outlet (24) and the second outlet (26). In order to make combination of the electrodes (30, 40) and the outlet (24, 26) easy, each electrode (30, 40) has a threaded head (32, 42) and each outlet (24, 26) has an inner thread to correspond to the threaded head (32, 42). Whereby, the electrodes (30, 40) are conveniently engaged with the cover (20) by means of screwing. Additionally, the working electrode (50) with a top face is placed inside the recess (12) and has a part of the working electrode (50) extending out from the recess (12). An inner lead (52) is attached on the top face and accommodated inside the O-ring (282) when the cover (20) is closed. An outer lead (54) is attached on the top face at the extending-out part to adapt to electrically connect with a readout system.

Figure 3:
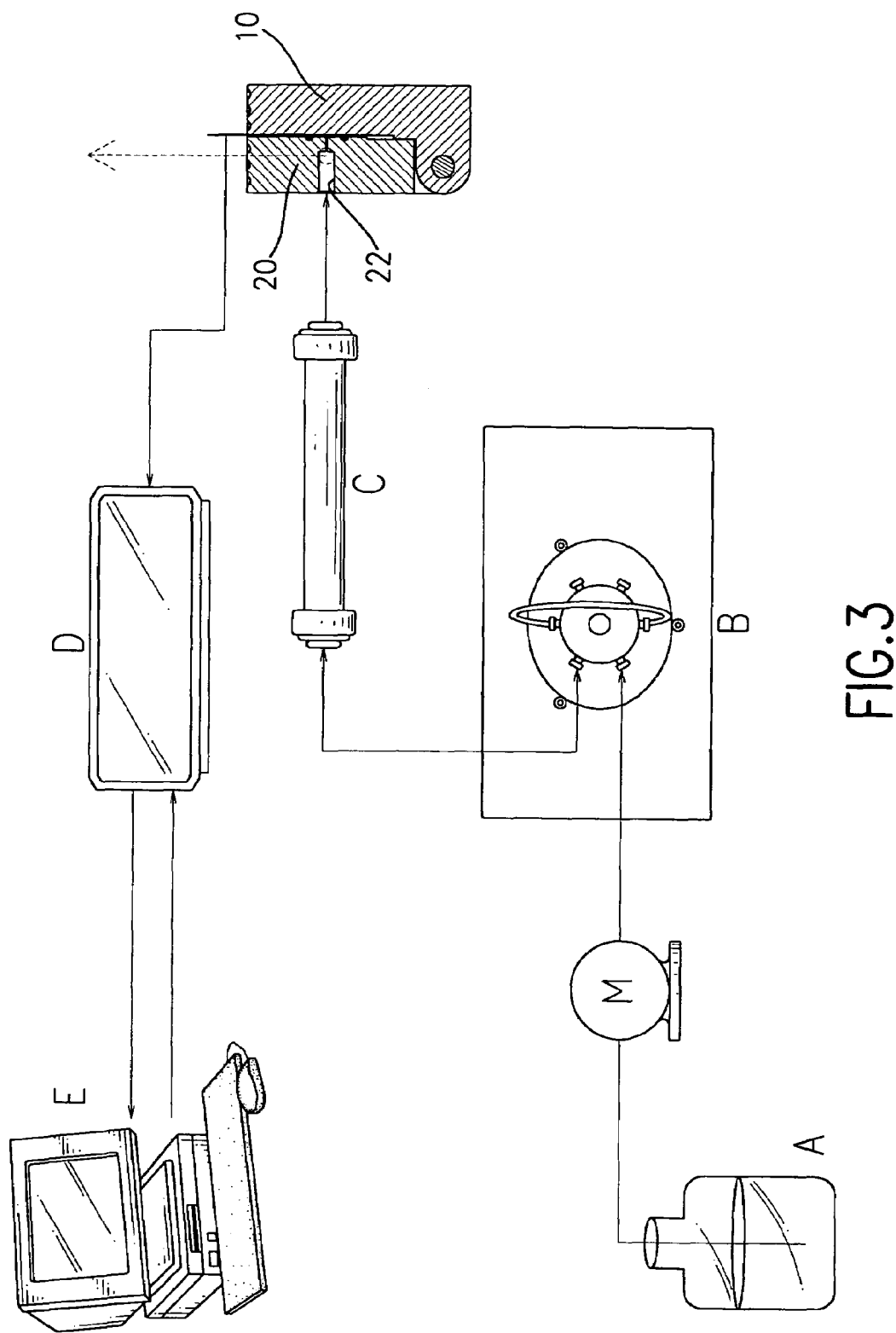
FIG. 3 is an operational side plane view of the flow injection electrochemical detecting device in FIG. 2.

With reference to FIGS. 3 and 4, when the flow injection electrochemical device operates, the liquid is transported to an injector (B) by a pump (M) from a storing bottle (A). The injector (B) provides a high pressure to make the liquid enter the space (a) via the inlet (22). Optionally, the liquid can be purified in an anion-exchange column (C) to remove impurity to avoid error when detecting. Lastly, the electrochemical data sensed by the working electrode (50) and the reference electrode (30) or the auxiliary electrode (40) are transmitted to an electrochemical workstation (D) to translate the data into readable information shown on a monitor (E).

With reference to FIGS. 5 to 8, the flow injection electrochemical detecting device in the present invention has a variety of operational embodiments in combination with the other accessory electrodes.

Figure 5:
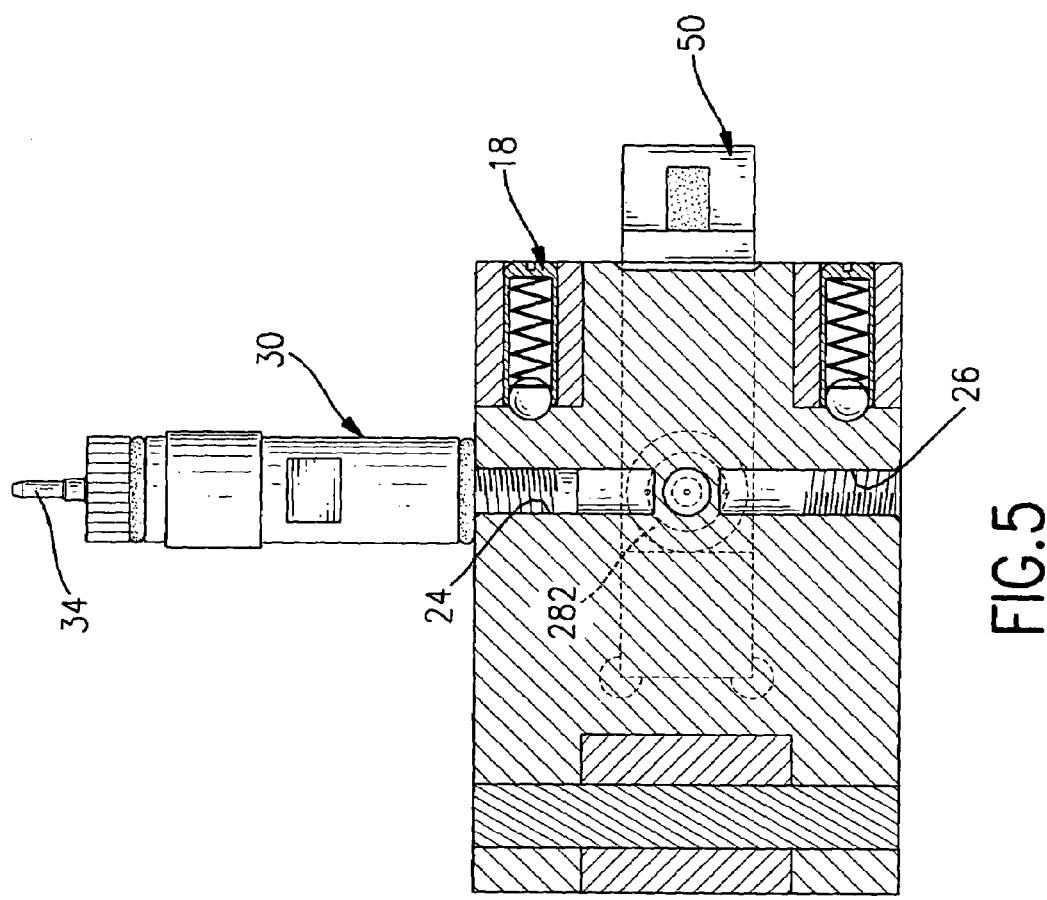
FIG. 5 is a cross-sectional top plane view of the flow injection electrochemical detecting device showing a first operating embodiment.

In FIG. 5, when the electrode (50) is a working electrode, the first outlet (24) has to engage with the reference electrode (30) and the second outlet (26) is kept as an opening channel to exhaust liquid.

Figure 6:
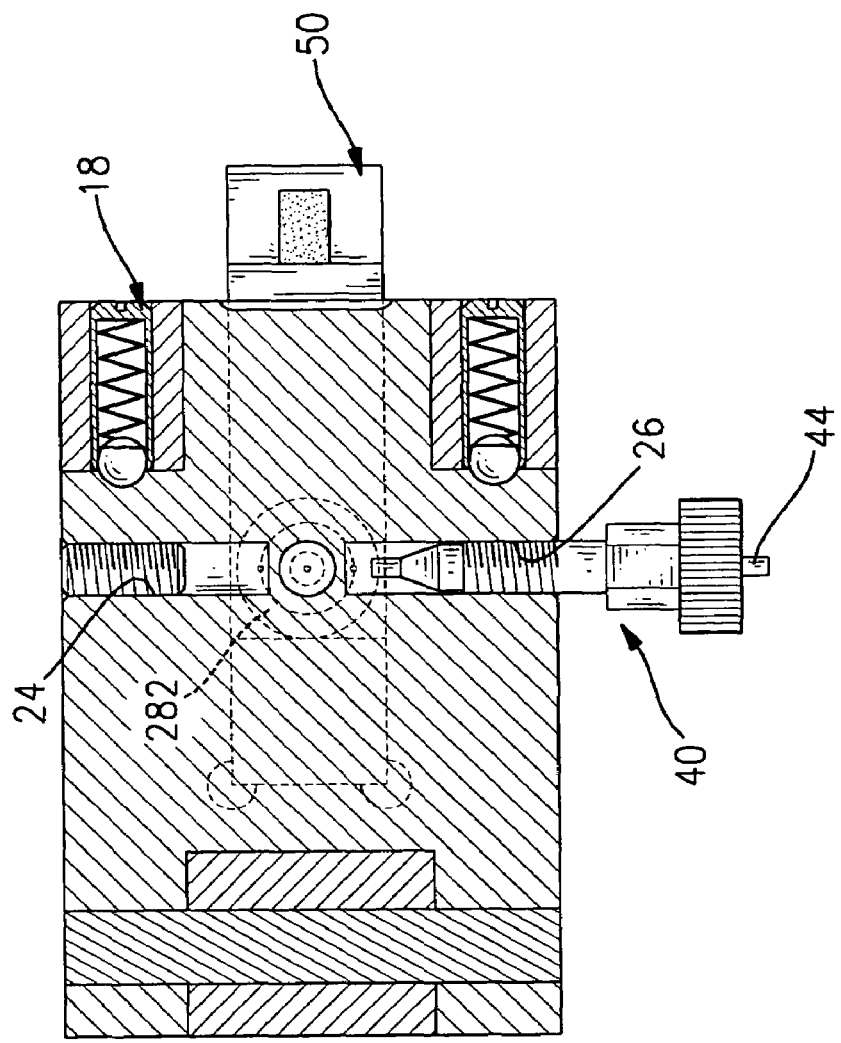
FIG. 6 is a cross-sectional top plane view of the flow-through electrochemical detecting device showing a second operating embodiment.

In FIG. 6, when the electrode (50) is a working electrode, the first outlet (24) selectively closes and the second outlet (26) has to engage with the auxiliary electrode (40), wherein the liquid flows out via the hollow first metal tube (44) in the auxiliary electrode (40).

Figure 7:
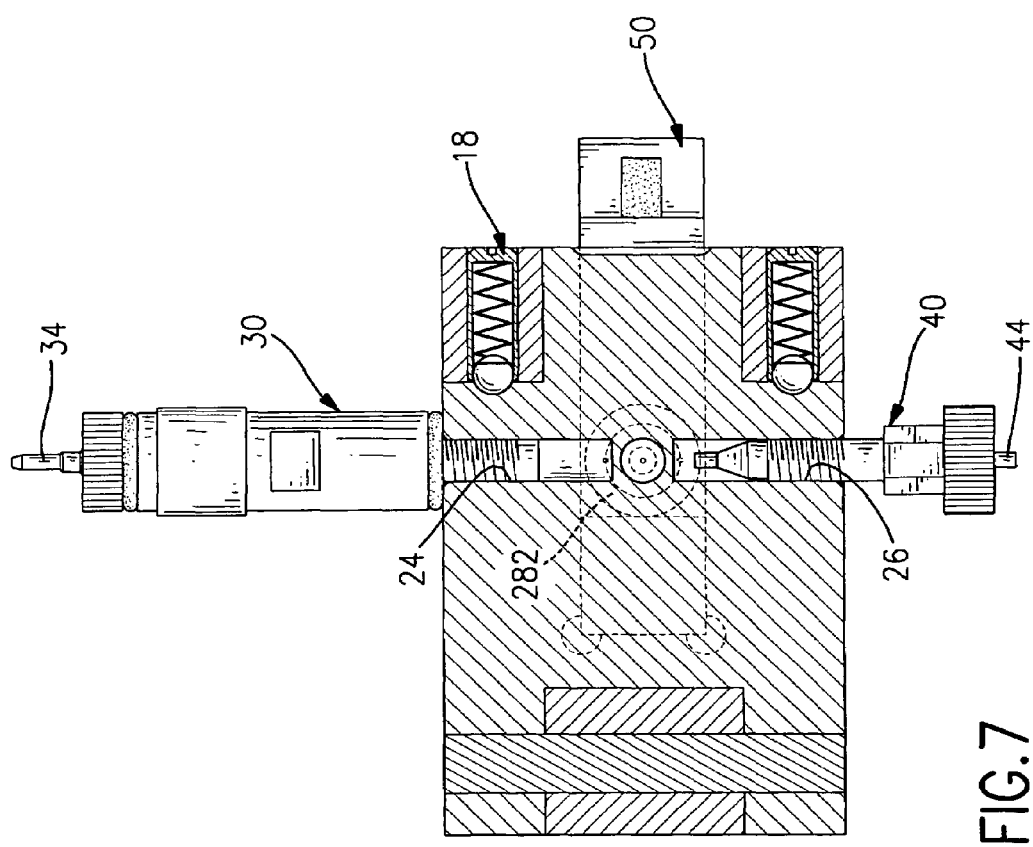
FIG. 7 is a cross-sectional top plane view of the flow injection electrochemical detecting device showing a third operating embodiment.

In FIG. 7, when the electrode (50) is a working electrode, the first outlet (24) selectively engages with the reference electrode (30) and the second outlet (26) selectively engages with the auxiliary electrode (40) to double check the electrochemical data. Wherein, the liquid flows out via the hollow first metal tube (44) of the auxiliary electrode (40).

Figure 8:
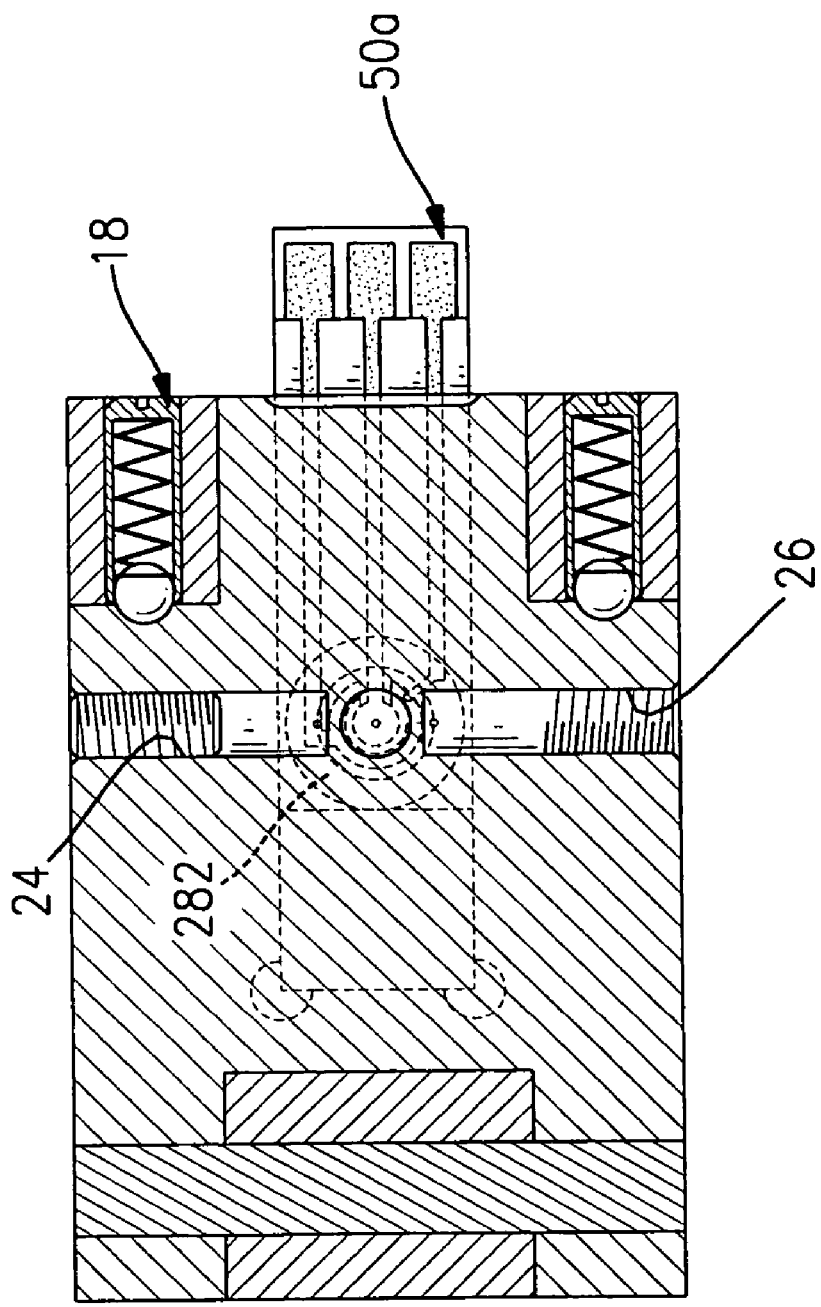
FIG. 8 is a cross-sectional top plane view of the flow injection electrochemical detecting device showing a fourth operating embodiment.
Figure 9:
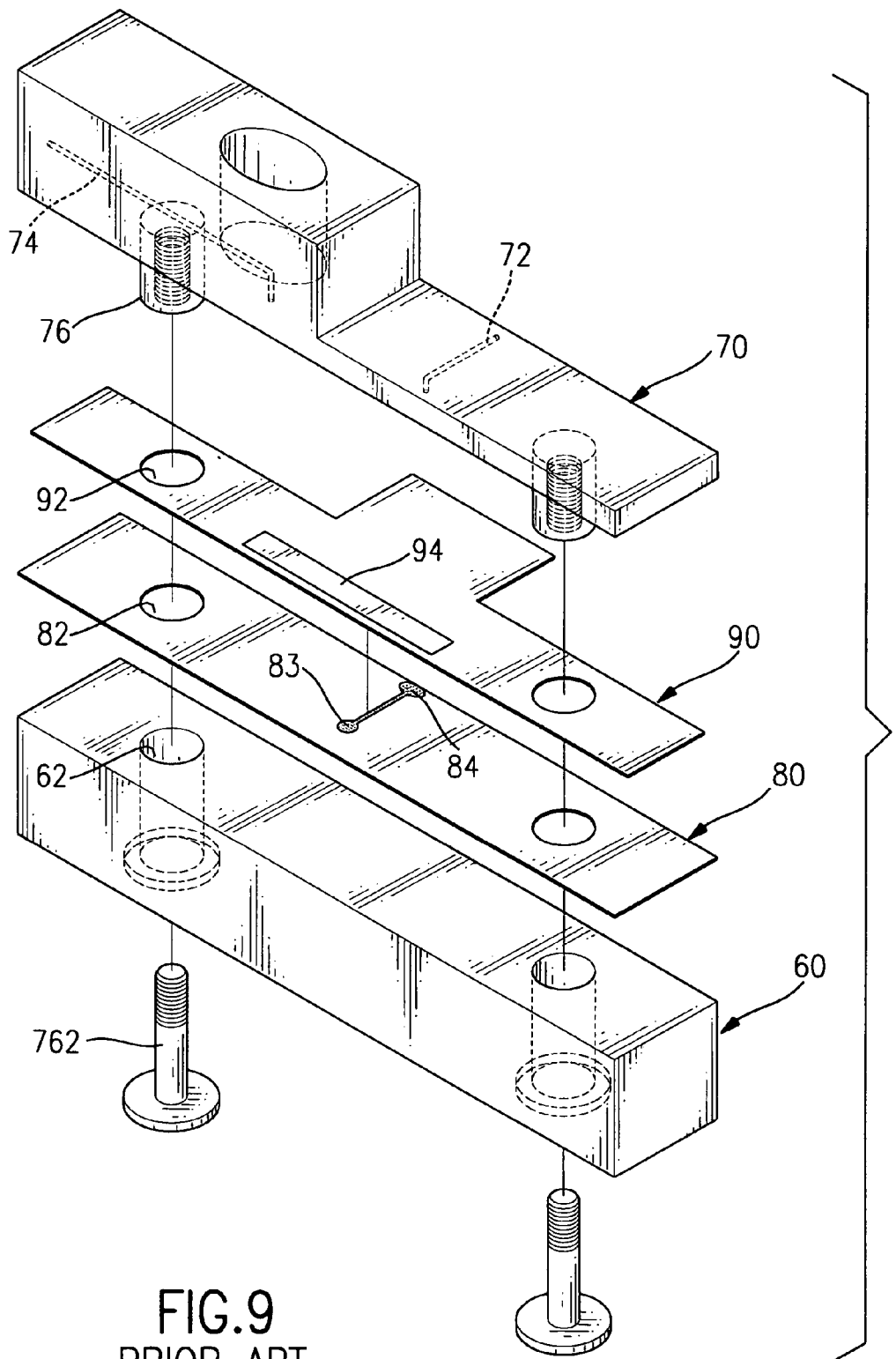
FIG. 9 is an exploded perspective view a conventional flow injection electrochemical detecting device in accordance with the prior art.

In FIG. 8, when the electrode is a three-electrode system (50a), no accessory electrodes are needed. The first outlet (24) closes and the second outlet (26) is kept as an opening channel to allow liquid to exhaust out from the device.

According to the above description, the flow injection electrochemical detecting device in the present invention is easily operated since the cover (20) pivotally detaches or engages with the base (10). Therefore, the working electrode (50) can be changed in a convenient way instead of disassembling all elements as shown in the conventional electrochemical detecting device.

Although the invention has been explained in relation to multiple preferred embodiments, many other possible modifications and variations can be made without departing from the spirit and scope of the invention as hereinafter claimed.

What is claimed is:

1. A flow injection electrochemical device comprising:
   a base (10) with a top, a front end, a rear end, and sides, and having a recess (12) defined in the top extending to the front end and a pivotal post (11) formed near the rear end;

a working electrode (50) being placed inside the recess (12);

a cover (20) with a top, a bottom, a front end, a rear end and two sides, which pivotally mounts on the base (10) and has a cutout (21) defined at the rear end to receive the pivotal post (11) of the base (10), a pin (111) penetrating the cover (20) at the cutout (21) and the pivotal post (11) to pivotally connect the cover (20) to the base (10), an annular trench (28) defined in the bottom of the cover, a resilient separator with an inner opening, which is an O-ring (282) and is partially mounted in the annular trench (28) of the cover (20), and multiple channels defined in the cover (20) and each having an opening at an area within the annular trench (28) to communicate with the inner opening of the resilient separator;

said cover (20) including a first outlet (24) and a second outlet (26) and an reference electrode (30) and auxiliary electrode (40) engaged within said first outlet and said second outlet respectively; and a locking device attached between the base (10) and the cover (20).

2. The flow injection electrochemical device as claimed in claim 1, wherein two ball dents (23) are defined at the front end of the cover (20); and the locking device comprises:

two locating posts (14) formed on the top of the base (10) at the front end and each of the two locating posts (14) having a threaded hole (142) defined through the locating post (14);

a threaded rod (18) screwing into the threaded hole (142) and having a bore (182) defined in the threaded rod (18);

a resilient element (184) accommodated inside the bore (182);

a ball (186) retractably mounted inside the locating post (14) and mounted on the resilient element (184) to detachably engage and lock with a ball dent (23).

3. The flow injection electrochemical device as claimed in claim 2, wherein the cover (20) further has two side cutouts (25) defined at the front end to match with the locating posts (14) and the two ball dents (23) are respectively defined in periphery of the two side cutouts (25).

4. The flow injection electrochemical device as claimed in claim 3, wherein the resilient element is a spring.

5. The flow injection electrochemical device as claimed in claim 1, wherein the multiple channels are:

an inlet (22) defined through the cover (20) from the top and having an opening (221) at the area within the annular trench (28);

a first outlet (24) defined in the cover (20) from one side and having an opening (241) at the area within the annular trench (28); and a second outlet (26) defined in the cover (20) from another side and having an opening (261) at the area within the annular trench (28).

6. The flow injection electrochemical device as claimed in claim 1, wherein the recess (12) is a dovetail recess having a width tapering toward the top of the recess (12).

7. The flow injection electrochemical device as claimed in claim 1, wherein the base (10) further has multiple grooves defined in the sides of the base to make the base easily held.

\* \* \* \* \*